United States Patent [19]

Fahmy

[11] Patent Number: 4,472,391
[45] Date of Patent: Sep. 18, 1984

[54] O-ARYL-S-(TERTIARY ALKYL) ALKYLPHOSPHONOTHIOATE INSECTICIDES AND NEMATOCIDES

[75] Inventor: Mohamed A. Fahmy, Princeton, N.J.

[73] Assignee: Rhone-Poulenc Agrochimie, Lyons, France

[21] Appl. No.: 369,555

[22] Filed: Apr. 19, 1982

Related U.S. Application Data

[63] Continuation of Ser. No. 209,094, Nov. 21, 1980, abandoned.

[51] Int. Cl.³ .................. A01N 57/2 L; C07F 9/40
[52] U.S. Cl. .................. 424/222; 260/940; 260/949; 260/951; 260/954; 260/955; 260/961; 424/210; 424/216; 424/217; 424/218; 424/219
[58] Field of Search .............. 260/961, 949, 940, 951, 260/954, 955; 424/219, 222, 218, 217, 216, 210

[56] References Cited

U.S. PATENT DOCUMENTS

| | | | |
|---|---|---|---|
| 2,934,507 | 4/1960 | Chadwick | 260/23 |
| 3,139,449 | 6/1964 | Ahramjian | 260/454 |
| 3,166,505 | 1/1965 | Kirby | 252/49.8 |
| 3,208,943 | 9/1965 | Kirby | 252/49.8 |
| 3,209,020 | 9/1965 | Schrader | 260/461 |
| 3,856,896 | 12/1974 | Hagarty | 260/956 |
| 3,919,362 | 11/1975 | Drabek | 260/961 |
| 4,257,987 | 3/1981 | Arend et al. | 260/956 |
| 4,284,626 | 8/1981 | Fahmy | 260/961 |
| 4,327,040 | 4/1982 | Arend et al. | 260/973 |

FOREIGN PATENT DOCUMENTS 3146056  6/1982  Fed. Rep. of Germany.

*Primary Examiner*—Anton H. Sutto
*Attorney, Agent, or Firm*—Burns, Doane, Swecker & Mathis

[57] ABSTRACT

Compounds having the formula

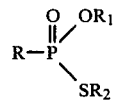

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms or haloalkynyl of 2 to 8 carbon atoms;
$R_1$ is aryl;
$R_2$ is tertiary alkyl of 4 to 8 carbon atoms; are disclosed as well as their use as insecticides and nematocides, e.g., in controlling corn rootworm and Southern Armyworm.

16 Claims, No Drawings

O-ARYL-S-(TERTIARY ALKYL) ALKYLPHOSPHONOTHIOATE INSECTICIDES AND NEMATOCIDES

CROSS-REFERENCE TO RELATED APPLICATIONS

This application is a continuation of application Ser. No. 209,094, filed Nov. 21, 1980 abandoned.

An application entitled "O-ARYL S-BRANCHED ALKYL ALKYLPHOSPHONODITHIOATE INSECTICIDES AND NEMATOCIDES", Ser. No. 108,329, filed Dec. 31, 1979 in the name of Mohamed A. Fahmy, discloses certain O-aryl-S-branched alkyl alkylphosphonodithioates.

SUMMARY OF THE INVENTION

This invention relates to O-aryl S-(tertiary-alkyl) alkylphosphonothioate compounds and their use as insecticides and nematocides.

More particularly, the compounds of the invention have the formula:

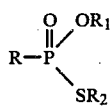

in which R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;

$R_1$ is aryl; and $R_2$ is tertiary alkyl of 4 to 8 carbon atoms.

These compounds exhibit a wide range of insecticidal and nematocidal activity and are of particular interest in controlling corn rootworm because of their excellent activity against this pest and their long residual soil activity.

DETAILED DESCRIPTION OF THE INVENTION

An important structural feature of the compounds of this invention is that $R_2$ in the above formula is tertiary alkyl. A variety of O-aryl S-alkyl alkylphosphonothioate insecticides are known in the art, such as in U.S. Pat. No. 3,209,020. However, applicant is aware of none which correspond to the above formula where $R_2$ is tertiary alkyl.

It has been found that the branched compounds of this invention possess unexpected advantageous properties. For example, they exhibit excellent stability and long residual activity particularly in soil and may desirably be employed in the control of the Southern Armyworm and corn rootworm. Since the activity of the tertiary compounds against corn rootworm is good and residual activity in soil is long, the compounds of this invention are of special interest for controlling corn rootworm.

The compounds disclosed herein can be prepared by the methods known to those in the art. Preferably, the compounds of this invention are prepared from a starting material which is S-(tertiary-alkyl) alkylphosphonothioic halide, the preparation of which is illustrated in Example 1.

The preferred reaction scheme is as follows:

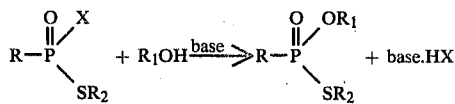

in which R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;

$R_1$ is aryl;

$R_2$ is tertiary alkyl of 4 to 8 carbon atoms; and

X is halogen, preferably Cl. Suitable aryl groups include phenyl and phenyl substituted with one or more alkyl of 1 to 4 carbon atoms, alkoxy of 1 to 4 carbon atoms, alkylthio of 1 to 4 carbon atoms, alkylsulfinyl of 1 to 4 carbon atoms, or alkylsulfonyl of 1 to 4 carbon atoms, Cl, Br, F, nitro, cyano, or trifluoromethyl, or combinations of the foregoing.

The tertiary alkyl group is preferably tert-butyl or tert-amyl.

The reaction is advantageously carried out at a temperature of about 0° C. to 100° C. in an organic solvent in the presence of a tertiary amine, aqueous base, such as aqueous NaOH, or by producing the alkali salt of the phenol using alkali metal salts such as sodium ethoxide Suitable organic solvents are, for example, benzene, toluene, cyclohexane, 2-butanone, and acetone Suitable tertiary amines include trimethylamine, triethylamine, dimethylaniline, diethylaniline and pyridine.

The alkylphosphonothioate compounds of this invention are effective as insecticides and/or nematocides at low concentrations. Because of the small amounts of the compounds required for effective control, it is generally impractical to apply the compounds directly as such. Therefore, it is desirable that the compounds be applied in the form of liquid compositions, or in combination with other vehicles or extenders.

The compositions containing the active compounds of this invention can be dispersions or emulsions. Since the active compounds are substantially water insoluble, it is desirable to add a small amount of an inert, nonphytotoxic organic solvent which can be readily dispersed in an aqueous medium to produce a uniform dispersion of the active component. For example, an effective liquid composition can be prepared with the active component, acetone or ethanol, water, and a surface-active agent such as Tween-20 (polyoxyethylene sorbitan monolaurate) or any of the other well known surface-active agents.

The compositions containing the active compounds can also be in powdered or granular form. For example, the active compound can be mixed with a suitable solid carrier such as kaolinite, bentonite, talc or the like, in amounts of about 5% to 20% by weight.

For the control of insects, the active ingredients are used at concentrations of from 0.01% to about 1% by weight of the total formulation. As nematocides, the active component is effective within the range of about 0.5 to 5 kg/hectare. Under ideal conditions, depending on the pest to be controlled, the lower rate may offer adequate protection. On the other hand, adverse weather conditions, resistance of the pest and other factors may require that the active ingredient be used in higher proportions.

When the pest is soil-borne, the formation containing the active ingredient is distributed evenly over the area to be treated in any convenient manner. The active component can be washed into the soil by spraying with water over the area or can be left to the natural action of rainfall. After application, the formulation can be distributed in the soil by plowing or disking. Application can be prior to planting or after planting but before sprouting has taken place or after sprouting.

The following examples illustrate the preparation of the compounds of this invention and their pesticidal properties. It will be understood that all of the compounds disclosed herein can be prepared by methods analogous to those described below.

EXAMPLE 1

S-tert-butyl ethylphosphonothioic chloride

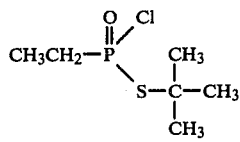

To a solution of ethylphosphonic dichloride (32.0 g, 0.22 mol) in 300 ml toluene, was added 2-methyl-2-propanethiol (18 g, 0.2 mol). While stirring triethylamine (22 g, 0.22 mol) was added dropwise and the temperature of the reaction was maintained at 30°–35° C. during the addition of the amine. After the complete addition of the amine, the mixture was stirred overnight at room temperature. The amine hydrochloride was filtered and the toluene solution was concentrated under vacuum. Hexane (200 ml) was added and the solution was filtered again.

The solvents were stripped off under vacuum and the residual liquid was distilled. The product (25 g, 72.5% yield) distilled at 72–73 C/0.7 mm. $^1$H-NMR in chloroform-d-Si(Me)$_4$ confirmed the structure of the title compound.

EXAMPLE 2

Preparation of O-phenyl-S-tert-butyl ethylphosphonothioate

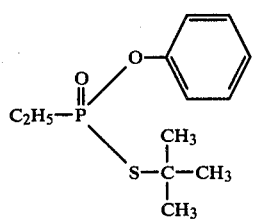

To a solution of S-tert-butyl ethylphosphonothioic chloride (5 g, 0.025 mol), and phenol (2.35 g, 0.025 mol) in 20 ml acetone, was added, in one portion, triethylamine (2.5 g, 0.025 mol), the mixture was stirred overnight under nitrogen at room temperature. The reaction mixture was diluted with toluene (100 ml) and washed once with 5% NaOH solution, and twice with water. The solution was dried over anhydrous sodium sulfate and the solvent was stripped off under vacuum. The residual liquid was subjected to high vacuum (0.2 mm) at 60° C. for 15 minutes to yield the desired product as confirmed by $^1$H-NMR spectrum in chloroform-d-Si(Me)$_4$.

EXAMPLES 3–10

In a manner analogous to that of Example 2, the following compounds were prepared.

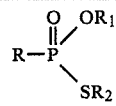

| Example | R | R$_1$ | R$_2$ |
|---|---|---|---|
| 3 | C$_2$H$_5$ | o-methyl-phenyl | tert-butyl |
| 4 | C$_2$H$_5$ | p-chloro-phenyl | tert-butyl |
| 5 | C$_2$H$_5$ | phenyl | tert-amyl |
| 6 | C$_2$H$_5$ | m-trifluoromethyl-phenyl | tert-amyl |
| 7 | C$_2$H$_5$ | p-fluoro-phenyl | tert-amyl |
| 8 | C$_2$H$_5$ | p-chloro-phenyl | tert-amyl |
| 9 | C$_2$H$_5$ | o-chloro-phenyl | tert-amyl |
| 10 | CH$_3$ | phenyl | tert-amyl |

A. Corn Rootworm Intrinsic Activity (CRw)

The test compound is prepared in a one percent solution with acetone or ethanol. The stock solution is then diluted with an aqueous solution of Tween-20 and water to the appropriate concentration (i.e., 500, 100, 1, 0.1, or 0.05 ppm). Two ml of this solution is pipetted into a 9 cm petri dish containing two layers of filter paper. Second instar larvae are introduced and the dish closed. Observations for mortality and moribund larvae are made after two days (48 hours) exposure. Insecticidal activity is primarily contact and vapor action with minimum ingestion. The results are tabulated in Table 1.

B. Southern Armyworm Intrinsic Activity (SAW)

The test compounds were also employed to determine the activity of the same against the Southern Armyworm and the results are set forth in Table 1.

TABLE I

| | % Kill | | | | |
|---|---|---|---|---|---|
| | SAW | | CRW | | |
| | Rate (ppm) | | | | |
| Example | 500 | 100 | 1 | 0.1 | 0.05 |
| 2 | 100 | 95 | 100 | 100 | 90 |
| 3 | 100 | 100 | 100 | 100 | 15 |
| 4 | 100 | 95 | 100 | 35 | 40 |
| 5 | 100 | 80 | 100 | 100 | 70 |
| 6 | 100 | 80 | 100 | 100 | 85 |
| 7 | 100 | 60 | 100 | 100 | 90 |
| 8 | 100 | 75 | 100 | 85 | 55 |
| 9 | 100 | 80 | 95 | 95 | 15 |

Although the present invention has been described with specific embodiments, it is to be understood that modifications and variations can be made without departing from the spirit and scope of this invention defined in the appended claims, as those skilled in the art will readily understand.

I claim:

1. A method for controlling insects and nematodes which comprises applying thereto or to their habitat a pesticidal amount of a compound of the formula

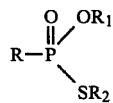

in which
- R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms or haloalkynyl of 2 to 8 carbon atoms;
- $R_1$ is phenyl or phenyl substituted with 1 or more members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano, and trifluoromethyl; and
- $R_2$ is a tertiary alkyl of 4 to 8 carbon atoms.

2. A method for controlling corn rootworm which comprises providing in the soil in an amount pesticidal to corn rootworm a compound of the formula:

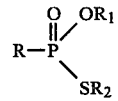

in which
- R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
- $R_1$ is phenyl or phenyl substituted with 1 or more members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano and trifluoromethyl; and
- $R_2$ is tertiary alkyl of 4 to 8 carbon atoms.

3. The method of claim 2 in which $R_1$ is phenyl.
4. The method of claim 2 in which R is alkyl of 1 to 8 carbon atoms.
5. The method of claim 2 in which R is methyl or ethyl; and $R_2$ is tert-butyl or tert-amyl.
6. The method of claim 2 in which
R is methyl or ethyl;
$R_1$ is phenyl; and
$R_2$ is tert-butyl or tert-amyl.
7. A composition comprising, as the active ingredient, a compound of the formula

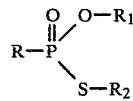

in which
- R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms or haloalkynyl of 2 to 8 carbon atoms;
- $R_1$ is phenyl or phenyl substituted with 1 or more members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano, and trifluoromethyl; and
- $R_2$ is a tertiary alkyl of 4 to 8 carbon atoms in an amount effective as an insecticide or nematocide;
and an inert, non-phytotoxic organic solvent or solid carrier.

8. The composition of claim 7 in which $R_2$ is tert-butyl or tert-amyl.
9. A compound of the formula

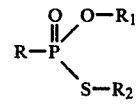

in which
- R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 9 carbon atoms or haloalkynyl of 2 to 8 carbon atoms;
- $R_1$ is phenyl or phenyl substituted with 1 or more members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano, and trifluoromethyl; and
- $R_2$ is tertiary alkyl of 4 to 8 carbon atoms.

10. A compound of claim 9 in which $R_1$ is phenyl.
11. A compound of claim 9 in which $R_2$ is tert-butyl or tert-amyl.
12. A compound of claim 9 in which R is alkyl of 1 to 8 carbon atoms.
13. A compound of claim 9 in which
R is methyl or ethyl;
$R_1$ is phenyl; and
$R_2$ is tert-butyl or tert-amyl.
14. A compound of claim 9 in which
R is ethyl;
$R_1$ is phenyl; and
$R_2$ is tert-butyl.
15. A compound of claim 9 in which
R is methyl or ethyl;
$R_1$ is methyl-phenyl; and
$R_2$ is tert-butyl or tert-amyl.
16. A compound of claim 9 in which
R is methyl or ethyl;
$R_1$ is chlorophenyl; and
$R_2$ is tert-butyl or tert-amyl.

* * * * *